United States Patent [19]

Kowalski

[11] Patent Number: 5,543,142
[45] Date of Patent: Aug. 6, 1996

[54] **METHOD FOR NATURALLY REGULATING PLANT GROWTH USING *ACTINOMYCES VISCOSUS***

[75] Inventor: William M. Kowalski, Houston, Tex.

[73] Assignee: Natural Industries, Inc., Houston, Tex.

[21] Appl. No.: 223,988

[22] Filed: Apr. 6, 1994

[51] Int. Cl.$^6$ .............................. A01N 63/00; C12N 1/12; C12N 1/20
[52] U.S. Cl. ...................... 424/93.4; 435/252.1; 435/826
[58] Field of Search ................................. 435/252.1, 826; 424/93 P, 93.4

[56] References Cited

U.S. PATENT DOCUMENTS

| | | | |
|---|---|---|---|
| 2,908,113 | 10/1959 | Martin | 47/58 |
| 5,157,207 | 10/1992 | Carlson et al. | 800/200 |

OTHER PUBLICATIONS

Kim, S. D. et al., "The Korean Biochemical Journal," vol. 23, #1, 1990, pp. 23–25.
Lechevalier, M. P., *Actinomyces in Biotechnology*, Academic Press, 1988, ed. Goodfellow, M., pp. 327–358.
Curtis, T., "The Old Man and the Secret", Texas Monthly, Jun. 1990, pp. 112, 114, 146–152.
Bryant, F. and H. Cutler, "Reductive Dechlorination of Pentachlorophenol by *Actinomyces Viscosus* Strain Dechlorini", American Chemical Society presentation, about Aug. 1992.
Natural Industries, Inc., Commercial labeling for Bloom'n Green Liquid Compost© 1992, a growth promoter distributed by Applicant, Fall 1992.
Black Gold Compost Co., Commercial labeling for Black Kow® Liquid Compost© 1990, a growth promoter distributed as liquid compost in late 1992.

*Primary Examiner*—Marian C. Knode
*Assistant Examiner*—Kristin Larson
*Attorney, Agent, or Firm*—Jennifer S Sickler; Jenkens & Gilchrist

[57] ABSTRACT

An improved method for regulating plant growth has been developed. The plant soil medium in which plants are grown is regulated to a pH in the range of about 2 to about 9, and preferably to a range of about 6.8 to 7.2. Then, *Actinomyces viscosus* strain GA is applied directly to the plant soil medium. The *Actinomyces viscosus*, GA delivers a natural biological control agent to plants, rather than a synthetic agent, which acts as a growth retardant and a flower initiator.

2 Claims, 2 Drawing Sheets

METHOD FOR NATURALLY REGULATING PLANT GROWTH USING *ACTINOMYCES VISCOSUS*

TECHNICAL FIELD

The present invention is a new method for growth regulation of plants. The plant soil medium in which plants are grown is regulated to a pH in a range between 2 to 9, and preferably to a range of about 6.8 to 7.2. Then *Actinomyces viscosus*, GA is applied directly to the plant soil medium. The *Actinomyces viscosus*, GA bacterium delivers a natural biological control agent to plants, rather than a synthetic agent, which acts as a growth retardant and flower initiator.

BACKGROUND

Plant growth regulators are chemicals used in some manner to alter the growth of plants, blossoms, or fruits. Hormones are the natural plant growth regulators produced by plants that, among other things, control growth, initiate flowering, cause blossoms to fall, cause fruit and leaves to fall, control initiation and termination of dormancy, and stimulate root development. Agricultural success depends, in large part, on external plant growth regulation to adapt the natural growth patterns of plants to the needs of the agricultural community.

The use and development of plant growth regulators began with the discovery that acetylene and ethylene would promote flowering in pineapples. This occurred in 1932, and by 1934, auxins were discovered to enhance root formation in cuttings. During the last 60 years, major discoveries in the area of plant growth regulators have resulted in the development of seedless fruits; the prevention of early, premature drop of fruits; the promotion of heavy setting of fruit blossoms; the prevention of sprouting in stored potatoes and onions; and the inhibition of buds in nursery stock and fruit trees to prolong dormancy.

The American Society for Horticultural Science recognizes six classes of plant growth regulators: auxins, gibberellins, cytokinins, ethylene generators, inhibitors, and growth retardants. The last class of regulator, growth retardants, includes an assorted group of substances that inhibit or retard certain physiological processes in plants. Two types of retardants have been developed for use: hormones and other substances that occur naturally in plants, and recently discovered, synthetic compounds. Examples of naturally occurring inhibitors in plants are benzoic acid, gallic acid, cynnamic acid, and (s)-abscisic acid. (s)-Abscisic acid, the most recently discovered naturally occurring hormone in plants, regulates gas exchange and water loss from plants.

Synthetic inhibitors include mepiquat chloride (Pix®), chlormequat chloride (Cycocel®), ancymidol (A-Rest®), dikegulac sodium (Atrinal®), daminozide (B-Nine®), and mefluidide (Embark®). Many of these synthetic growth inhibitors inhibit the synthesis of gibberellins, which results in the slowing or halting of elongations of leaves and stems, both in grasses and broad leaf plants.

A variety of synthetic plant growth retardants, such as Alar®, Bonzi®, and A-Rest® have been used previously in commercial settings to prevent plants from becoming overgrown. These chemicals are toxic to humans, however, at relatively low concentrations, and some are suspected carcinogens. Consequently, these retardants are not labelled for commercial application on food-producing plants and are under scrutiny in the ornamented plant industry.

The use of plant growth retardants and flower initiators in the commercial plant-growing industry is critical to the economic well-being of the industry. However, the use of such agents by the industry is limited, since many synthetic chemicals are either no longer in use due to their suspected carcinogenic effect or toxicity, or because they are not approved for certain types of plants. Naturally occurring hormones in plants, moreover, cannot be harvested economically and are too expensive for large scale use. The impact of such restrictions is that entire crops may be lost due to seasonal variations, for example, rain, that delays planting. Thus, a plant growth regulator is greatly needed by the industry that is safe, available in large quantities, and economical to use.

SUMMARY OF THE INVENTION

The present invention is directed to a new method for growth regulation of plants using *Actinomyces viscosus*, GA. The method for growth regulation involves regulating the pH of a plant soil medium to a pH range of about 2 to 9; and applying *Actinomyces viscosus*, GA directly to the plant soil medium. In the most preferred method, the pH is adjusted to a range of about 6.8 to 7.2 and most preferably is about 7.0.

It is an object of the present invention to provide a natural biological control agent for growth retardation or flower initiation of plants. The method of use of the growth retardant of this invention has an advantage over the prior art in that it is environmentally friendly and does not have the adverse health effects exhibited by many synthetic agents. The bacterium used in the present invention delivers a natural biological control agent to plants when applied to a plant soil or synthetic medium at a pH range of about 2 to 9.

It is another object of the present invention to provide a plant growth retardation and/or flower initiation method that is as effective as or more effective than the synthetic products commercially available. Field tests indicate that the effects of *Actinomyces viscosus*, GA exceeds that of Alar® and Bonzi®.

Still other objects, features and advantages of the present invention will be apparent from the following description of the preferred embodiments given for the purpose of disclosure and taken in conjunction with the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE PREFERRED METHOD

Figure 1:
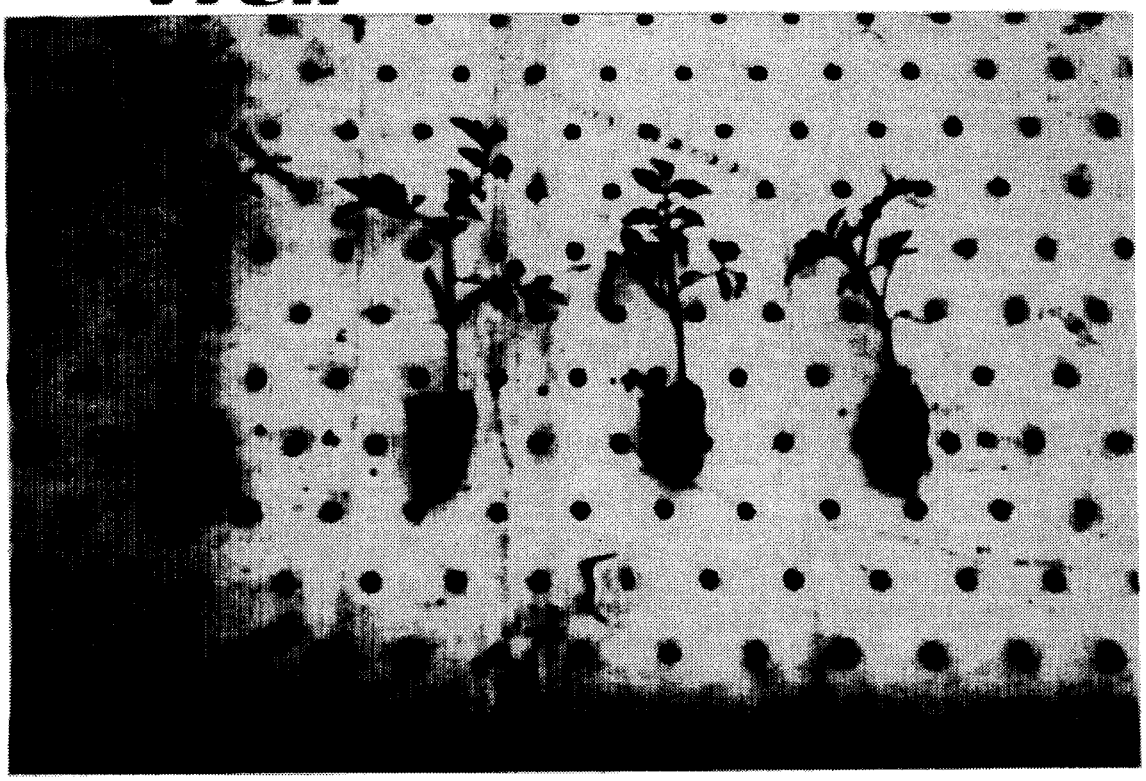
FIG. 1 is a photograph of Sunny tomato plants showing the effect of growth regulator treatment with, from left to fight, a control solution, Alar®, *A. viscosus*, GA, and Bonzi®.
Figure 2:
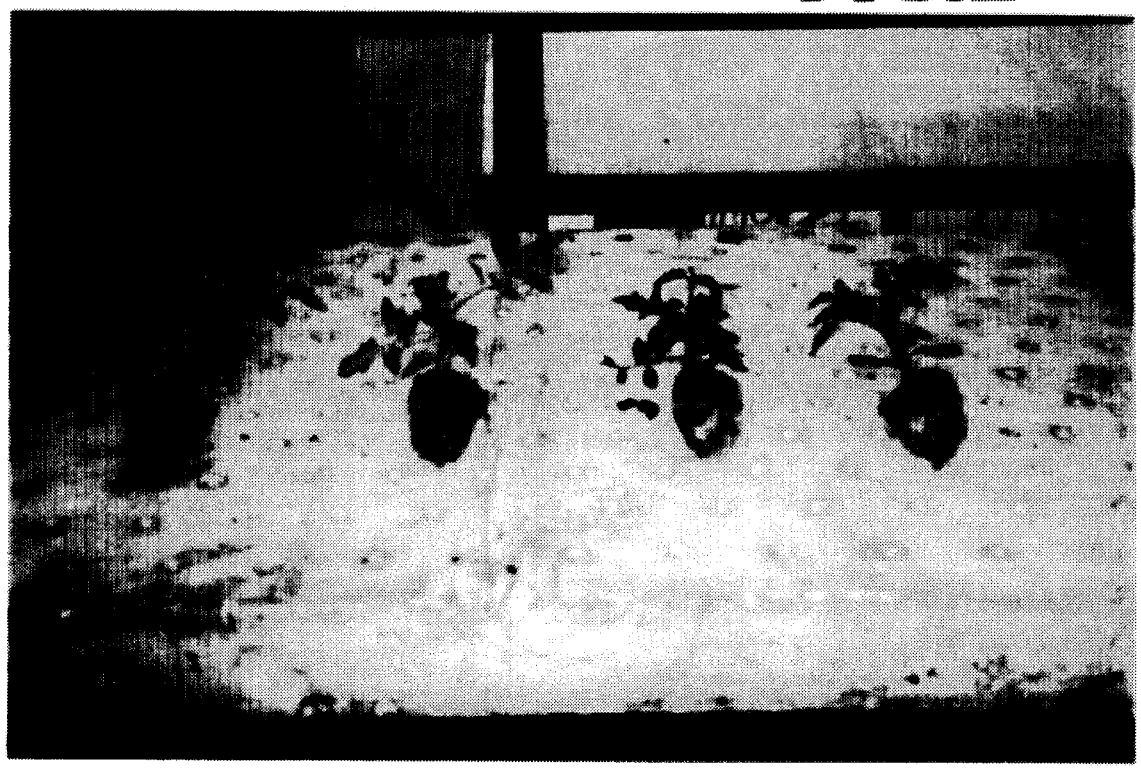
FIG. 2 is a photograph of Cherry tomato plants showing the effect of growth regulator treatment with, from left to fight, a control solution, Alar®, *A. viscosus*, GA, and Bonzi®.
Figure 3:
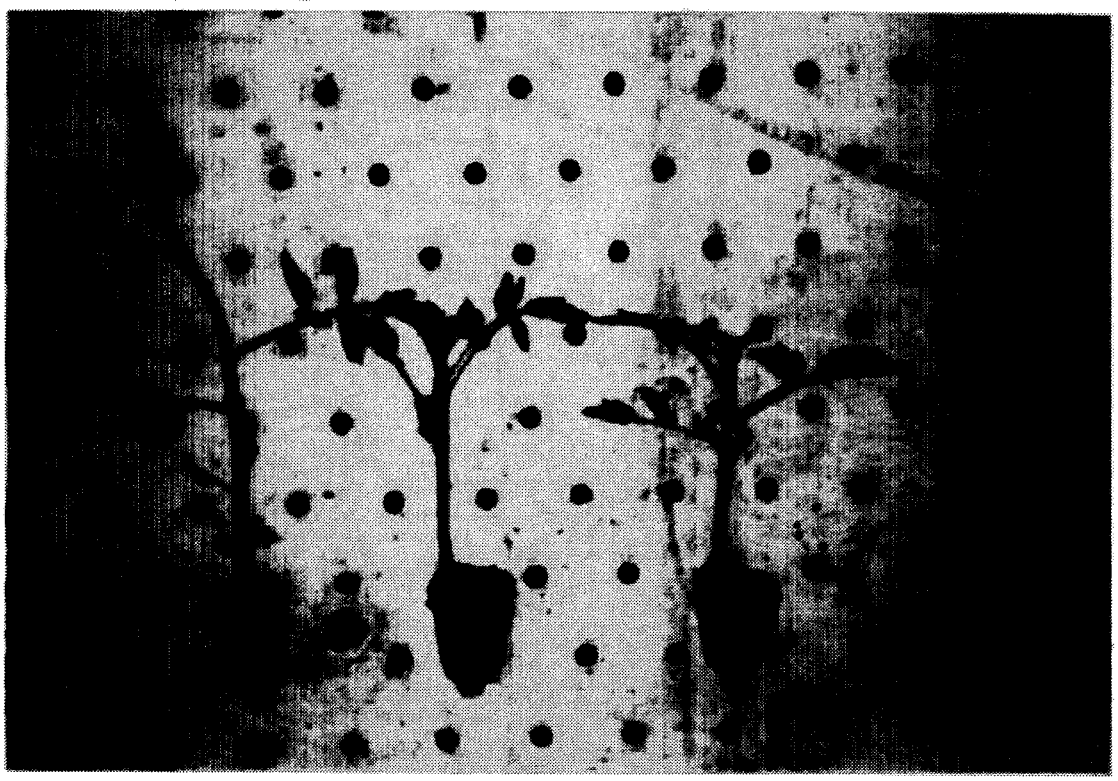
FIG. 3 is a photograph of Cherry tomato plants showing the effect of growth regulator treatment with, from left to fight, a control solution, Alar®, *A. viscosus*, GA, and Bonzi®.
Figure 4:
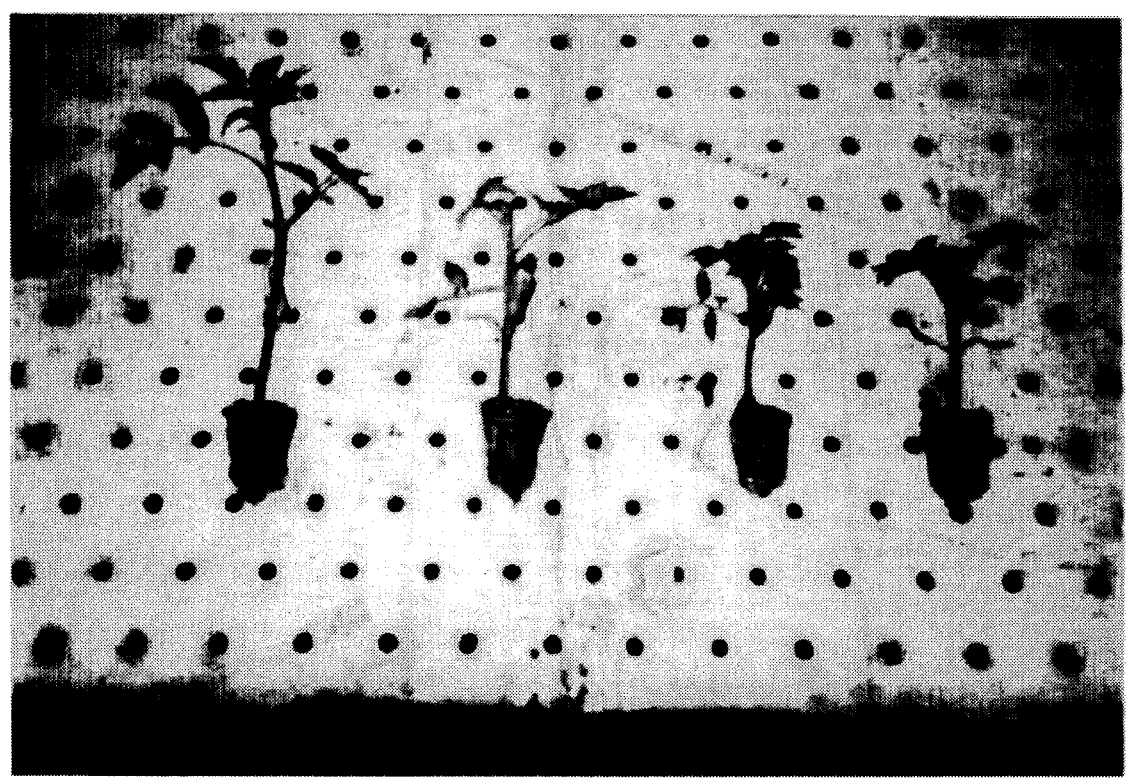
FIG. 4 is a photograph of Olympic tomato plants showing the effect of growth regulator treatment with, from left to fight, a control solution, Alar®, *A. viscosus*, GA, and Bonzi®.

The method involves a couple of steps which generally include adjusting the pH of a plant soil medium to a range of about 2 to 9, on an as needed basis; and then applying *Actinomyces viscosus*, GA to the plant soil medium. A preferred pH range is from about 6.8 to about 7.2 and, in the most preferred embodiment, the pH of the plant soil medium is adjusted to about 7.

A preferred bacterium has been deposited with the American Type Culture Collection (ATCC), an approved International Depository Authority, at 12301 Parklawn Drive, Rockville, Md. 20852. The *Actinomyces viscosus*, GA was deposited on Oct. 18, 1994 and was accorded ATCC No. 55624. The bacterium *Actinomyces viscosus* strain, GA may also be purified from fermented cow manure, preferably from lactating cows. Cow manure, preferably from lactating cows, is collected. In one preferred method, about 5 gallons of cow manure is added to a large volume of nonchlorinated water. The ratio of cow manure to water may vary greatly. In the preferred method, the volumetric ratio of manure to water is in a range of 1:100 to 1:1,000. Thus, about 5 gallons of cow manure is added to about 5,000 gallons of water, in one preferred method.

The manure solution is thereafter anaerobically fermented in a tank or similar device that is air tight. The New Brunswick Scientific Mobile Pilot Plant is a workable fermentor, for example. Small quantities of yeast extract may be added to the manure solution to promote bacterial growth, but is not necessary. A yeast extract powder that may be used is Catalog No. 103303 by ICN Biomedicals, Inc., Aurora, Ohio. The fermentation time may vary considerably, but the longer the manure solution ferments, the more bacterial growth will occur. In the preferred method, the solution is fermented for about 5 to 10 days, and most preferably for about 7 days.

Following, anaerobic fermentation, the manure solution is transferred to a tank or similar device that allows for aeration of the solution. Aerobic fermentation is then allowed to occur for about 2 days or more. There is no upward limit on the aerobic fermentation time. However, in the preferred method, aerobic fermentation lasts from about 2 to about 10 days. During aerobic fermentation, the manure solution preferably is aerated and agitated constantly. Aeration may occur at a rate in the range of about 2% to about 10% air on a volumetric basis. Agitation may be performed by a paddle agitator, but other devices may be used for agitation, as are well known to those skilled in the art. The rate of agitation is in the range of about 100 to 200 rpm in the preferred method. Most preferably, the rate of agitation is about 140 rpm.

As a result of anaerobic and aerobic fermentation, the bacteria existing at the end of the fermentation periods should be facultative bacteria. In addition, the bacteria should preferably have a cell count of at least $10^3$/ml.

The manure solution is then centrifuged at speeds and times well-known by those skilled in the art. The speed and time of centrifugation are selected to accomplish separation of most of the liquid solution from the bacteria. The supernatant is decanted and discarded, and the precipitant bacteria may be preserved as a supply of the *Actinomyces viscosus* GA.

Specifically, once a bacterial extract of the cow manure is obtained, purification of the bacterium may be accomplished by serial dilution using a buffered yeast glucose solution. In one preferred embodiment of the invention, the serial dilution requires two dilutions involving one percent (1%) transfers through 10 serum-stoppered bottles. One preferred medium for the dilution is as follows: 1.5 g/l $KH_2PO_4$, 1.5 g/l $K_2PO_4$, 0.5 g/l $NH_4Cl$, 4.2 g/l $Na_2HPO_4 \cdot 12 H_2O$, 0.18 g/l $MgCl_2 \cdot 6 H_2O$, 2.0 g/l yeast extract (Difco), and 8.0 g/l glucose. This medium is preferably prepared under strict anaerobic conditions using the "Hungate" technique. This purified bacterial solution may be referred to as the "starter solution".

Once a starter solution of the bacteria has been made, it can be used to grow larger volumes of the bacteria. For example, it is practical to prepare the medium in batches of 200 ml. The gas phase used is purified air (filtered with a 0.2 micron filter to remove bacteria). Compressed air may be purchased from Big 3 Industries, Inc., Houston, Tex. To prepare 200 ml of the medium, the above medium ingredients are dissolved in about 190 ml of distilled water. The medium is autoclaved at about 120° C. for about 20 minutes at about 15 psi to 18 psi (15 psi is preferred). An autoclave that may be used is Scientific Equipment Manufacturing Corporation (New York, N.Y.), Model No. 1016. Inoculation is done microaerophillically under aseptic conditions with a syringe from either a growing culture (i.e., a starter solution) or a culture that has been properly stored. About 10 ml of the culture is used for inoculation. The inoculated medium is then incubated at about 37° C. for about 72 hours. An incubator that may be used is a gravity convector anaerobic incubator by GCA Corporation. At that point the 200 ml of bacterial culture has been grown to a cell count of about $10^9$ cells/ml.

To create a larger volume of the bacterial culture, a 10 liter carboy or similar device should be filled with 9.8 liters of the buffered yeast glucose solution described above. This solution is autoclaved at about 120° C. and about 15 psi for about 20 minutes. The solution is then cooled to 37° C. on a desktop preferably. It may be stored in a dark place. Inoculation is done microaerophillically under aseptic conditions with, preferably, the 200 ml culture just grown. Inoculation may be done by forcing air into an opening of the 200 ml vessel, thus forcing the liquid culture to exit from the 200 ml vessel through a second opening to then travel through a tube to the 10 liter carboy. The inoculated medium is then incubated at about 37° C. for about 72 hours. At that point, 10 liters of bacteria has been grown to a cell count of about $10^9$ cells/ml.

To create an even larger volume of the bacterial culture, in the preferred method, a 400 liter fermentor is filled with about 390 liters of the buffered yeast glucose solution described above. This solution is autoclaved at about 120° C. and about 15 psi for about 20 minutes. The solution is then cooled to about 37° C. on a desktop, preferably. Inoculation is then done microaerophillically under aseptic conditions with, preferably, the 10 liter carboy of culture just grown. The inoculated medium is then incubated at about 37° C. for 96 hours. During this incubation, the solution is agitated with preferably a paddle agitator at a rate in the range of about 120 to about 160 rpm. In addition, air is sparged into the culture solution at a rate, preferably, of about 2% air on a volumetric basis. Following the incubation, the culture cell count should be about $10^9$ cells/ml of the culture.

At this point, the culture may be harvested and packaged for commercial use, or larger volumes of the culture may be grown by repeating the steps outlined above with some minor changes to accommodate the larger volumes. Such changes in procedure would be known to those skilled in the art, and involve changes such as time of incubation, rate of aeration, and rates of agitation.

Harvesting may be accomplished by opening a valve at the bottom of the fermenting tank and transferring the culture to sterilized containers aseptically. The containers would then be sealed with air tight lids for shipment or storage for later use. The average shelf life of the bottled culture is generally at least one year.

In one alternate method of the invention, *Actinomyces viscosus* strain, GA is grown to a final volume of about 14 liters in a 16 liter New Brunswick Microgen (SF-116) benchtop fermentor. Initially, 10 ml of the buffered yeast glucose medium identified above is distributed into each of a number of 20 ml screw-capped culture tubes. The tubes are vented by loosening the caps and then autoclaved for about 20 minutes at about 121° C. and about 15 psi. The medium in the tubes is then cooled to room temperature and used immediately. Inoculation of the medium with the bacterium is performed using sterile technique with 0.1 ml from a growing 10 ml culture of the bacterium. The culture is vented by loosening the screw-cap and placed in an incubator at about 32° C. for a time period of about 24 to 48 hours. Cultures reach a final cell count of about $10^9$ cells/ml. One of these tubes may used to create a 200 ml culture.

Next, a 200 ml culture of the bacterium may be prepared as the inoculum for a 16 liter fermentor. In this larger volume sample, 200 ml of medium is placed in a 500 ml sponge-stoppered flask and autoclaved for about 20 minutes at about 121° C. and about 15 psi. Upon cooling to room temperature, the medium is inoculated with a 10 ml culture, prepared as described above, and incubated at about 32° C. for a time period of about 24 to 48 hours. This culture is used as an inoculant for the 16 liter fermentor when cell counts reach a concentration of about $10^9$ cells/ml.

A 16 liter fermentor is then filled with about 14 liters of medium. The lid to the fermentor should be a kind that allows for venting. The 16 liter fermentor is autoclaved for about 20 minutes at about 121° C. and about 15 psi. The medium in the fermentor is then cooled to room temperature and inoculated with the above-prepared 200 ml culture. This culture is incubated at about 32° C. for a time period of about 24 to 48 hours.

The *A. viscosus*, GA culture is ready to use on plants when the cell count reaches a range of above about $10^6$ cells/ml. Preferably, the cell count is at least $10^9$ cells/ml. Higher cell counts are even more preferable.

Following the purification procedure described above, the bacterium may be subjected to systematic tests to confirm its identify, including procedures for testing special characteristics, performed in accordance with D. Gottlieb, *Bergey's Manual of Determinative Bacteriology*, pp. 657–681 (8th ed., The Williams & Wilkins Co., 1974); and P. Geardt, et al., *Manuals of Methods for General Bacteriology*, pp. 333, 358–359, 409–443 (American Society for Microbiology, 1981).

For identification purposes, it may be helpful to know that the bacterium grows under both anaerobic and aerobic conditions, indicating that it is a facultative anaerobe. Microcolonies grow aerobically within 24 hours on potato dextrose agar (PDA) at 37° C., displaying a dense core and filamentous (spidery) appearance at the periphery. Liquid cultures initially display filamentous cells of various lengths and branching. As the culture grows, the filaments eventually fragment into coccoid cells and finally form mucoid aggregates that appear as a flocculent mass in the medium. The bacteria appears to display pleomorphic growth.

Tests for spores are negative so far, although coccoid cells are refractile in appearance. Spore tests may be performed such as the "popping test", the "Scaeffer-Fulton method" and the "Dornor Method" for staining endospores.

These findings are consistent with classification of the bacterium within the family Actinomycetaceae in the genus Actinomyces. See T. Cross, et al., *Actinomycetales: Characteristics and Practical Importance*, pp. 11–21 (Academic Press 1973). Assignment of the bacterium to the species *viscosus* may be confirmed by a positive catalase reaction. See L. K. Georg, et al., *Inter. J. Syst. Bacteriol.*, Vol. 19, pp. 291–93.

The *Actinomyces viscous* produces an exocellular biological control agent that serves as the plant growth retardant. Testing may be done to confirm that the biological control agent is exocellular, i.e., produced by the bacterium and secreted into the surrounding environment. A test to confirm this may be conducted as follows: a culture of the bacterium (1 liter, $10^8$ cells/ml, 12.4 mm coleoptile) is centrifuged at 11,000×g for two hours, decanted and centrifuged again at 11,000×g for 90 minutes. The resultant supernatant solution upon bioassay is found to be inhibitory. The resuspended pellet, in contrast, displays a coleoptile growth comparable to experimental controls.

The bacterium and its secreted biological control agent are sensitive to extremes of pH. At pH extremes of about 2 or less and about 9 or more, the biological control agent does not function as a growth retardant. At pHs between 2 and 9, however, the bacterium and biological control agent have a growth retardant function. One preferred pH range is from about 6 to about 8. The most preferred pH is about 7.

Once sufficient volumes of the bacteria culture have been grown, the *Actinomyces viscosus*, GA is applied to plant soil mediums. In the most preferred method of this invention, all application and solvent delivery systems are buffered with phosphate salts to a pH of approximate neutrality of 7.0. However, the pH may be regulated to a range of about 2 to 9, or, more preferably, to a range of about 6.8 to 7.2. In one preferred method, approximately 8 oz. of the live *A. viscosus*, GA culture is mixed with 25 gallons of delivery solution (approximately 1:500 dilution). The delivery solution may be water or any other liquid medium suitable for plants, including a fertilizer solution. This mixture of culture and delivery solution may be referred to as the bacterial solution or the delivery system. This dilution is applied to accomplish an application rate in the range of about 0.5 oz. to about 16 oz. bacterial culture per 100 square feet of flats of growing plants on a weekly basis. A more preferred rate of application is in the range of about 1 oz. to about 4 oz. bacterial culture per 100 square feet of plants, on a weekly basis. When applying the bacterial solution to the plant soil, moreover, the soil should be thoroughly saturated. Thus, another factor for determining the concentration of the delivery system is how wet or dry the soil medium is. The drier the soil, the more dilute the delivery system should be and the higher the application rate should be. In colder weather, moreover, the bacterial solution generally needs to be applied more often and at a higher concentration.

Numerous other dilutions of the bacterial culture are also suitable for treating plants, depending upon the circumstances, as will be well-known by those skilled in the art. For example, a dilution of 2 oz. of live culture per 100 ft$^2$ of plants has proved successful for growth regulation of bell peppers. Dilutions of 4 oz. of live culture per 100 ft² of hot pepper plants and 1 oz. of live culture per 100 ft² of tomato plants have also been successful. The dilution ranges and application rates provided are meant to be instructive but not limiting.

The following example is provided to facilitate the understanding of preferred methods of the present invention and not for the purpose of limiting same. Those skilled in the art will recognize the various modifications and the procedure previously discussed and outlined below to be used for the purpose of practicing the new present invention.

EXAMPLE 1

In an experiment involving one preferred method and consisting of three different cultivars of tomatoes (Cherry, Sunny, and Olympic), all fertilizer application and water systems were buffered with phosphate salts at a pH of approximate neutrality, pH 7.2. Approximately 8 oz. of the live *A. viscosus*, GA was mixed with 25 gallons of delivery solution. This bacterial solution was applied to the tomatoes at a rate of either 2 oz. or 4 oz. culture per 100 $ft.^2$ of flats of growing plants. Two flats (each containing about 325 plants) of each cultivar of tomatoes, with one of the two being treated with extra fertilizer, were used. Two flats of each cultivar were treated separately with one of the following: (1) *A viscosus,* GA (2 oz. conc.); (2) *A viscosus,* GA (4 oz. conc.); (3) Alar® (B-Nine®) at the recommended rate; (4) Bonzi® (at 2 ppm); (5) Bonzi® (at 4 ppm); or (6) non-treated control solution. Otherwise, each flat of plants was delivered the same amount of fertilizer, water, and other controls. A representative sample of the results of treatment about 24 days after treatment are shown in FIGS. 1 through 4.

FIGS. 1 through 4 show a significant difference between all cultivars of the control plants and those treated with *A. viscosus*, GA. The control plants were typically leggy, light green and not suitable for transfer to the field. By comparison, the cultivars treated with the *A. viscosus*, GA were dwarfed in appearance, dark green to purple, thicker in the stem region and were ready for transfer to the field. Cultivars treated with Alar® had an appearance similar to the controls. Cultivars treated with Bonzi® were similar in appearance to those treated with the bacterium. Importantly, however, the bacterium application produced a plant that was slightly shorter, thicker in the stem and displayed a shorter distance between the node and cotyledon. No differences occurred due to the differences in fertilizer application rates.

EXAMPLE 2

In additional experimentation involving another preferred method, 40 tomato plants, and 40 pepper plants were administered an *A. viscosus*, GA solution at rates of 0.0, 0.5, 1.0, and 2.0 oz. culture per 100 $ft^2$ of flats of growing plants. The *A. viscosus*, GA delivery solution consisted of 8 oz. of the live bacteria mixed with 25 gallons of delivery solution. Each flat of plants was delivered the same amount of fertilizer, water and other controls. The results of the tests are summarized in TABLE I below.

TABLE I

| PLANT | PLANT FEATURE | CULTURE APPLN. × RATE OZ./100 $ft^2$ of flats | NO. OF REPETITIONS | MEAN MEASUREMENT |
|---|---|---|---|---|
| Tomato | Stem Length | 0.0 | 10.0 | 16.540 cm |
| | | 0.5 | 10.0 | 12.800 cm |
| | | 1.0 | 10.0 | 10.030 cm |
| | | 2.0 | 10.0 | 8.820 cm |
| | Fresh Top Weight | 0.0 | 10.0 | 2.211 g |
| | | 0.5 | 10.0 | 2.002 g |
| | | 1.0 | 10.0 | 1.608 g |
| | | 2.0 | 10.0 | 1.584 g |
| | Fresh Root Weight | 0.0 | 10.0 | 0.7785 g |
| | | 0.5 | 10.0 | 0.6684 g |
| | | 1.0 | 10.0 | 0.5772 g |
| | | 2.0 | 10.0 | 0.5650 g |
| | Leaf Area | 0.0 | 10.0 | 27.744 $cm^2$ |
| | | 0.5 | 10.0 | 25.096 $cm^2$ |
| | | 1.0 | 10.0 | 20.811 $cm^2$ |
| | | 2.0 | 10.0 | 18.784 $cm^2$ |
| | Dry Top Weight | 0.0 | 10.0 | 0.2661 g |
| | | 0.5 | 10.0 | 0.2452 g |
| | | 1.0 | 10.0 | 0.2028 g |
| | | 2.0 | 10.0 | 0.1992 g |
| Pepper | Stem Length | 0.0 | 10.0 | 12.550 cm |
| | | 0.5 | 9.0 | 12.200 cm |
| | | 1.0 | 10.0 | 11.520 cm |
| | | 2.0 | 10.0 | 11.170 cm |
| | Fresh Top Weight | 0.0 | 9.0 | 1.1518 g |
| | | 0.5 | 10.0 | 1.0183 g |
| | | 1.0 | 10.0 | 0.9250 g |
| | | 2.0 | 10.0 | 0.9087 g |
| | Fresh Root Weight | 0.0 | 10.0 | 0.8052 g |
| | | 0.5 | 10.0 | 0.8000 g |
| | | 1.0 | 9.0 | 0.7970 g |
| | | 2.0 | 10.0 | 0.7607 g |
| | Leaf Area | 0.0 | 9.0 | 25.277 $cm^2$ |
| | | 0.5 | 10.0 | 22.824 $cm^2$ |
| | | 1.0 | 10.0 | 19.475 $cm^2$ |
| | | 2.0 | 10.0 | 18.103 $cm^2$ |
| | Dry Top | 0.0 | 9.0 | 0.16682 g |

TABLE I-continued

| PLANT | PLANT FEATURE | CULTURE APPLN. × RATE OZ./100 ft² of flats | NO. OF REPETITIONS | MEAN MEASUREMENT |
|---|---|---|---|---|
| | Weight | 0.5 | 10.0 | 0.15156 g |
| | | 1.0 | 10.0 | 0.13014 g |
| | | 2.0 | 10.0 | 0.12571 g |

These test results show reduced plant height (stem length), fresh top weight, fresh root weight, leaf area, and dry top weight, as the application rate of the *A. viscosus*, GA solution increases. For both tomatoes and peppers, the bacterial solution was delivered at a control rate of 0.0, which allowed the most plant growth. Increased growth retardation occurred with each increase in solution application rate from 0.5 to 1.0 to 2.0 culture oz. per 100 ft² of flats of growing plants. Mean measurements for each group of plants are shown in the last column of TABLE I. Nine or ten repetitions were performed for each solution application rate for each plant feature (e.g., stem length).

EXAMPLE 3

The following example is one preferred embodiment of the present invention for hibiscus (variety "Sheri") plants. Thirteen ounces of *Actinomyces viscosus*, GA was added to 50 gallons of fertilizer solution. The fertilizer solution is one commonly available on the market and its composition is not relevant to the result of the application of the bacteria solution to the plants. This mixture was then injected into the irrigation system of 50,000 plants at a rate of 1 part *A. viscosus*, GA/fertilizer mixture to 200 parts water. The water was at a pH of about 7.0. The procedure was repeated weekly during the growing season.

The control set of plants that were previously grown under the same conditions, including the same commercial fertilizer produced one bloom per plant at a time. With the application of *A. viscosus*, GA as described above, each plant exhibited multiple blooms.

Those skilled in the art, upon reading the above detailed description of the present invention, will appreciate that many modifications of the method described above can be made without departing from the spirit of the invention. All such modifications which fall within the scope of the appended claims are intended to be covered thereby.

We claim:

1. A method for retarding plant growth by *Actinomyces viscosus* GA (ATCC#55624) comprising the steps of:
   (a) adjusting the pH of a plant soil medium containing plants to a range of about 6 to about 8; and
   (b) applying a growth retarding effective amount of *Actinomyces viscosus* GA (ATCC#55264) to said plants.

2. A method for initiating flowering in plants using *Actinomyces viscosus* GA (ATCC#55624) comprising the steps of:
   (a) adjusting the pH of a plant medium containing plants to a range of about 2 to about 9; and
   (b) applying a flower initiating effective amount of *Actinomyces viscosus* GA (ATCC#55264) to said plants.

* * * * *